(12) United States Patent
Johnson

(10) Patent No.: US 9,482,599 B1
(45) Date of Patent: Nov. 1, 2016

(54) WATER TESTING METHOD AND APPARATUS

(71) Applicant: Lyle Johnson, Fort Lauderdale, FL (US)

(72) Inventor: Lyle Johnson, Fort Lauderdale, FL (US)

( * ) Notice: Subject to any disclaimer, the term of this patent is extended or adjusted under 35 U.S.C. 154(b) by 22 days.

(21) Appl. No.: 14/311,226

(22) Filed: Jun. 20, 2014

(51) Int. Cl.
| | |
|---|---|
| *G01N 1/10* | (2006.01) |
| *G01N 33/18* | (2006.01) |
| *G01N 1/44* | (2006.01) |
| *G01G 19/00* | (2006.01) |
| *G01N 5/00* | (2006.01) |
| *G01N 27/02* | (2006.01) |

(52) U.S. Cl.
CPC .............. *G01N 1/10* (2013.01); *G01G 19/00* (2013.01); *G01N 1/44* (2013.01); *G01N 5/00* (2013.01); *G01N 27/02* (2013.01); *G01N 33/18* (2013.01); *G01N 33/1813* (2013.01)

(58) Field of Classification Search
CPC ..... G01N 33/18; G01N 33/1813; G01N 1/10
USPC .......................................................... 374/14
See application file for complete search history.

(56) References Cited

U.S. PATENT DOCUMENTS

| | | | |
|---|---|---|---|
| 4,125,376 A | 11/1978 | Razulis | |
| 4,678,559 A * | 7/1987 | Szabados | ................ G01N 1/28 209/17 |
| 4,871,662 A * | 10/1989 | Rosov | .............................. 435/30 |
| 5,059,319 A * | 10/1991 | Welsh | .................... B01D 29/01 210/232 |
| 5,215,659 A * | 6/1993 | Ando | ........................ C02F 1/68 210/282 |
| 5,306,087 A | 4/1994 | Nakamura | |
| 5,886,898 A * | 3/1999 | Choudhury | ............ G06Q 10/08 379/100.11 |
| 7,172,729 B2 | 2/2007 | Las Navas Garcia | |
| 8,038,942 B2 | 10/2011 | Pang | |
| 2002/0092362 A1 | 7/2002 | Tonge | |
| 2006/0102550 A1 * | 5/2006 | Joseph | .................. B05B 7/2408 210/464 |
| 2010/0043129 A1 * | 2/2010 | Platteel et al. | ..................... 4/300 |
| 2012/0040436 A1 * | 2/2012 | Harada et al. | ................. 435/219 |

FOREIGN PATENT DOCUMENTS

GB          2389357 A   * 12/2003   ........... A61K 9/0065

OTHER PUBLICATIONS

Odhner et al, "A compliant, underactuated hand for robust manipulation", Feb. 17, 2014, The International Journal of Robotics Research, vol. 33(5), pp. 736-752.*

* cited by examiner

*Primary Examiner* — Hezron E Williams
*Assistant Examiner* — David Z Huang
(74) *Attorney, Agent, or Firm* — Oltman, Flynn & Kubler

(57) ABSTRACT

An automated water testing apparatus and to a method of using the apparatus to test the amounts of dissolved salts and other solids in a water sample, where the apparatus includes a specially constructed sample bottle which preferably has a flexible wall and is fitted with a filter cap having a mesh top wall through which sample water can be poured to remove suspended matter, several beakers, a desiccator enclosure, a computer containing a database and an inventive computer program for executing method steps, and several devices in communication with and controlled by the computer and the program for executing the method, these devices preferably including a conductivity meter having a meter electrode, a robotic arm having a gripper, an analytical scale, a top loader balance scale and an oven.

11 Claims, 6 Drawing Sheets

WATER TESTING METHOD AND APPARATUS

BACKGROUND OF THE INVENTION

1. Field of the Invention

The present invention relates generally to the field of environmental monitoring. More specifically the present invention relates to an automated water testing apparatus and to a method of using the apparatus to test the amounts of dissolved salts and other solids in a water sample to meet the requirements of the Clean Water Act, found at 40 C.F.R. 136 and the Safe Drinking Water Act, found at 40 C.F.R. 141. The apparatus includes a specially constructed sample bottle which preferably has a flexible wall and is fitted with a screw-on removable filter cap having a mesh top wall through which sample water can be poured to remove suspended matter including organics and plant matter, at least one and preferably several receiving vessels preferably in the form of beakers, and a desiccator enclosure. The apparatus further includes a computer containing a database and an inventive computer program for executing most or all of the method, and several devices designed to be connected to the computer so that they are controlled by and relay data to the computer such as through a two-way bus. These devices preferably include a conductivity meter having a meter electrode, a robotic arm having a gripper, an analytical scale, a top loader balance scale and an oven.

The method, in summarized form, includes but is not limited to the steps of: providing the above apparatus; one of a person and the computer through operation of the robotic arm delivering a sample of water to be tested into the sample bottle and securing the filter cap onto the bottle; the computer operating the robotic arm to lift and place the conductivity meter electrode into the sample water and activating the conductivity meter to perform a test to determine the concentration of salt in the sample water; the computer operating the robotic arm gripper to grasp the bottle, to hold it over at least one and preferably sequentially over several receiving vessels such as a beakers, and to tilt the bottle to a sufficient angle from vertical and for a sufficient duration to pour a selected quantity of sample water through the filter cap and into each beaker; and the computer operating the gripper of the robotic arm to squeeze the plastic sample bottle at least one time to force water otherwise obstructed by suspended matter through the filter cap sequentially into each beaker; the computer operating the robotic arm to cause the gripper placing the beakers one at a time onto the scale; the scale automatically relaying to the database and recording the weight of each successive beaker and the water it contains, and the program subtracting the known tare weight of each beaker to determine the water sample weight within each beaker, until at least two successive weights of each given beaker match; placing the beakers into the oven between weighings; the computer operating the robotic arm to cause the robotic arm to place the beaker into the oven; the computer causing the oven to activate and heat the beakers to a first temperature for a first period of time until the water in the beakers is fully evaporated, leaving only solid residue from the sample water in each of the beakers, which may include a substantial quantity of salt; the computer operating the robotic arm to remove the beakers from the oven and to place them one at a time on the scale; the scale relaying the beaker and solids residue weight to the computer such that the weight data is stored in the database; the computer program calculating the ratio of solids to water by weight and displaying, storing and printing the ratio such as in milligrams per liter or in parts per million (ppm). The results of this total dissolved solids (TDS) test reveal whether the water sample meets EPA requirements of a maximum of 500 mg per liter for drinking water.

The squeeze force applied by the gripper to squeeze the sample bottle preferably is in a range of 1 to 7 pounds. Squeeze force at the higher end of this range is applied where there is a high concentration of suspended matter in the sample water, causing flow resistance through the filter cap mesh. The amount of squeezing is not determined by displacement. In pouring sample water into each beaker, the computer detects the weight of the beaker on the scale in real time, such that the computer knows when the given beaker has received the desired quantity of sample water whereupon the computer causes the robotic arm and gripper to stop pouring from the sample bottle.

Applicant has discovered that a suitable robotic arm that is produced by ST ROBOTICS™. Yet applicant found that the gripper provided with this robotic arm is not suitable for performing steps of the present invention, and therefore found it necessary to replace it with a different gripper made by another manufacturer, ROBOTIQ™ of Canada, for another purpose. The ROBOTIQ™ gripper is intended for gripping eggs. This gripper has an intuitively variable gripping and squeezing force and provides variable opening and closing speed. The grippers of other known robotic arms simply open and close with a fixed force and at a fixed speed. The several devices designed to be connected to the present computer can both read and write, incorporating a two-way bus. Each device sends data signals back to the computer and the computer sends signals to the device to control its operation.

Key inventive features include the squeezable sample bottle with the filter cap, the use of a robotic arm and gripper for tilting and squeezing the bottle, which is made possible by the use of the inventive bottle filter, preferably embodied in the filter cap, the synergy of the combination of these apparatus elements, the method steps, and the program itself which executes much of the inventive method.

2. Description of the Prior Art

There has long been water testing equipment and procedures for using the equipment.

Nakamura, et al, U.S. Pat. No. 5,306,087, issued on Apr. 26, 1994, discloses an apparatus for thermogravimetry. Nakamura, et al., provides a computer operated robotic arm which lifts sample containers on and off a thermobalance which weighs the containers empty and then full, and then subtracts the container weight. The steps performed, however, are not intended to meet and fall short of what is required for testing according to the above mentioned water quality Acts, such as conductivity testing to determine salt content and filtration to remove suspended solids and organics.

Razulis, U.S. Pat. No. 4,125,376, issued on Nov. 14, 1978, teaches a method for detecting water pollutants through the use of a sampling test tube containing a foam cube impregnated with a detection chemical solution. Once again, this method and apparatus fall far short of meeting the requirements of the Acts, as do the following prior patents. Tonge, et al., U.S. Patent Application Publication Number 2002/0092362, published on Jul. 17, 2002, reveals a flow-metering and sampling catch basin insert, providing means for isolating water entering a catch basin or manhole from flows from other catch basins so that the flow rate and water quality for water entering the catch basin can be measured without contamination. Las Navas Garcia, U.S. Pat. No. 7,172,729, issued on Feb. 6, 2007 discloses a mixed sample moisture or ash analyzer which uses a robotic arm to retrieve a crucible from a conveyor and to insert the crucible into a small opening in an upper wall of a furnace, placing it on a carousel inside the furnace. This patent does not address the requirements of water quality analysis. Finally, Pang, et al., U.S. Pat. No. 8,038,942, issued on Oct. 18, 2011, teaches an automated sample processing system involving the handling of biological specimen containers such as to perform centrifugation and decapping.

It is thus an object of the present invention to provide a water testing apparatus and method of using the apparatus which is largely or entirely automated to an extent that unattended operation is achieved and human operators are no longer necessary.

It is another object of the present invention to provide such a method which is largely or wholly executed by a computer and produces reliable results and meets government standards and requirements.

It is still another object of the present invention to provide such an apparatus includes an inventive sample bottle with a filter cap and makes new use of a robotic arm with a gripper, making such automation possible.

It is yet another object of the present invention to provide such an apparatus and method which employee use with only minimal training.

It is finally an object of the present invention to provide such an apparatus which provides greater precision with greater quality and which is safe and inexpensive enough to be practical.

SUMMARY OF THE INVENTION

The present invention accomplishes the above-stated objectives, as well as others, as may be determined by a fair reading and interpretation of the entire specification.

A water testing apparatus is provided, including a sample bottle fitted with a removable cap having cap rim and having a filter comprising filter mesh; at least one testing vessel; a desiccator enclosure; a computer containing a database and water testing computer program in operational communication the database; a computer operated robotic arm having a gripper in communication with the computer; a computer operated conductivity meter having a meter electrode and in communication with the computer; a computer operated scale for recording and storing weights in the computer database; and a computer operated oven in communication with the computer.

The filter mesh preferably is incorporated into the removable cap. The testing vessels preferably are beakers. The filter mesh is nominal, average size, preferably substantially 2 micron size. The at least one testing vessel preferably is a plurality of testing vessels. The testing vessels preferably are beakers. The at least one scale preferably is at least one of an analytical scale and a top loader balance scale. The sample bottle preferably is sized to contain 250 cubic centimeters. The sample bottle preferably is formed at least in part of polyethylene.

A method of testing water is provided to determine concentrations of dissolved solids, comprising the steps of: providing the testing apparatus; one of a person and the computer operated robotic arm delivering a first water sample into the sample bottle and securing the filter cap onto the sample bottle; the robotic arm grasping the meter electrode and inserting the electrode into the water sample; the conductivity meter relaying sample water conductivity data to the database; the robotic arm sequentially placing the at least one of clean beakers into the oven; the computer signaling the oven to heat to a first temperature for a first length of time to thereby evaporate any moisture on or within the beakers; the robotic arm removing the beakers from the oven; the robotic arm placing the beakers sequentially into the desiccator enclosure; the robotic arm placing the beakers one at a time onto the analytical scale to transmit to the database and record the tare weight; the robotic arm placing each tared beaker on the scale one at a time; the robotic arm lifting the sample bottle and moving the sample bottle toward a first one of the beakers on the scale; the robotic arm moving the sample bottle to mix the water sample; inverting the sample bottle over the first one of the beakers; the robotic arm gripper then proportionately squeezing the sample bottle while the computer monitors the weight of the beaker and sample water as the sample water enters the first beaker; the gripper discontinuing the sample bottle squeezing once a desired volume of sample water is reached in the first beaker; the computer operating the robotic arm to sequentially repeat these beaker filling steps to fill a plurality of additional beakers; the computer operating the robotic arm to grip, lift and place the beakers into the oven; the computer operating the oven to increase its internal temperature to a second temperature for a second length of time to evaporate the water from the beakers, thereby heating the beakers and the residue within the beakers to the second temperature and permitting the beakers to remain heated at the second temperature until all of the water in the beakers has evaporated; and then heating the oven to a third temperature for a third length of time; the robotic arm removing the beakers from the oven; and placing the beakers into the desiccator enclosure to cool to the temperature of the balance itself; the robotic arm placing the beakers one at a time onto the scale; the scale transmitting the weights of each successive beaker and its corresponding contained residue to the database; the computer calculating the net weight of the residue in each beaker by subtracting the tare weight of the corresponding beaker; the computer calculating the quantity of total dissolved solids from the net weight and volume for each beaker; the computer repeating the weighings of each beaker to obtain constant weights according to stored criteria for each beaker; and, once the constant weight criteria is met for each beaker, the computer using the most recent weight to calculate the final total dissolved solids and storing and recording the final total dissolved solids for each beaker in the database.

The scale preferably is at least one of an analytical scale and a top loader balance scale. The volume of sample water for the test preferably (in milliliters) is substantially 25000/conductivity in micromhos. The first temperature preferably is substantially 105 degrees Celsius. The first length of time preferably is substantially two hours. The second temperature preferably is 98 degrees Celsius for the second length of time, which is however long is needed for the beakers to become completely dry, and normally is several hours. Then the oven temperature is raised to the third temperature of 180 degrees Celsius for the third length of time of one hour to drive off any occluded moisture. The calculation of total dissolved solids (TDS) from the net weight and volume taken preferably is made according to the formula: TDS (mg/1=(A−B)×1000/sample volume (in grams).

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
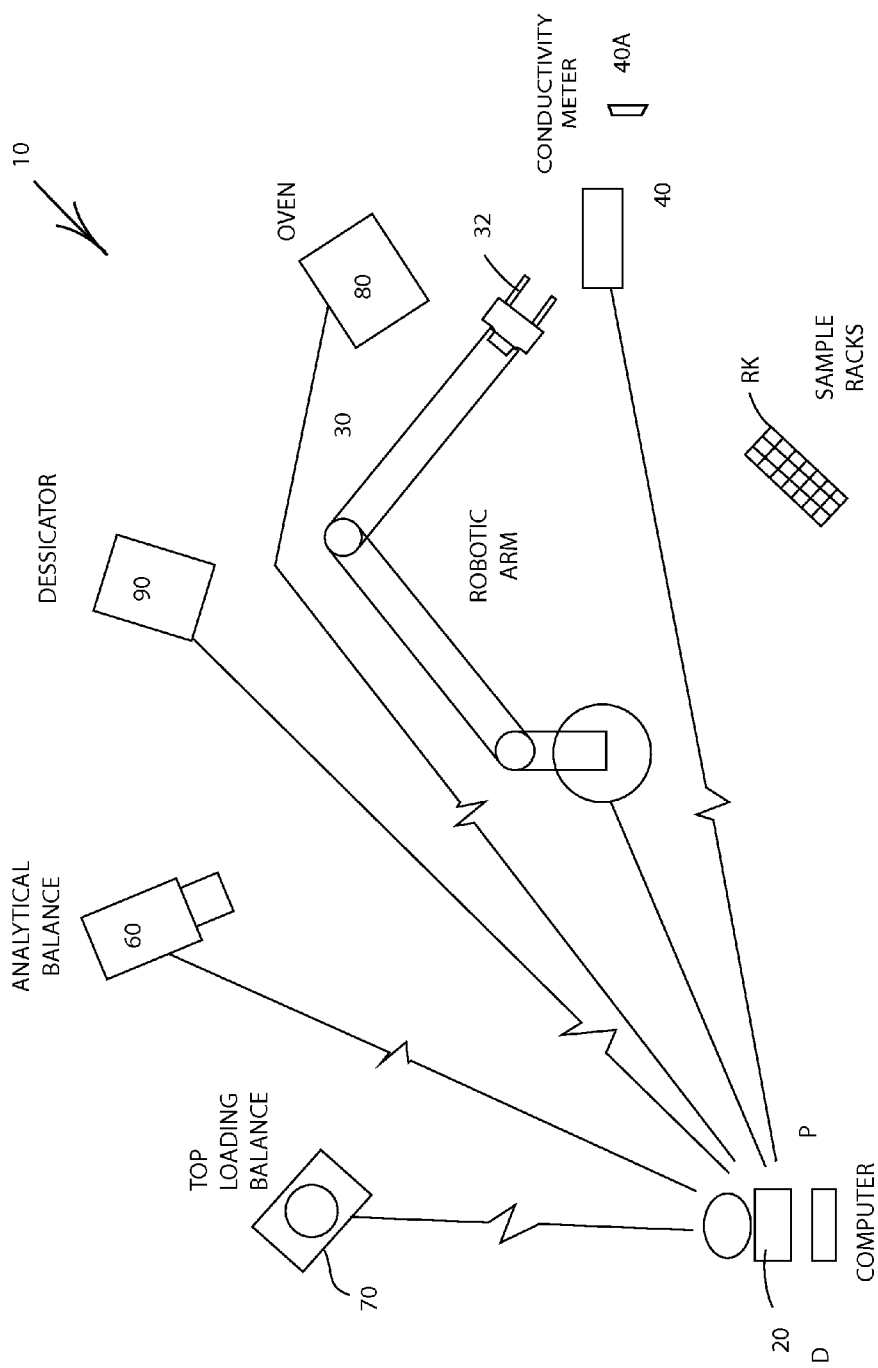
FIG. 1 is a schematic view of the preferred water testing apparatus.
Figure 2:
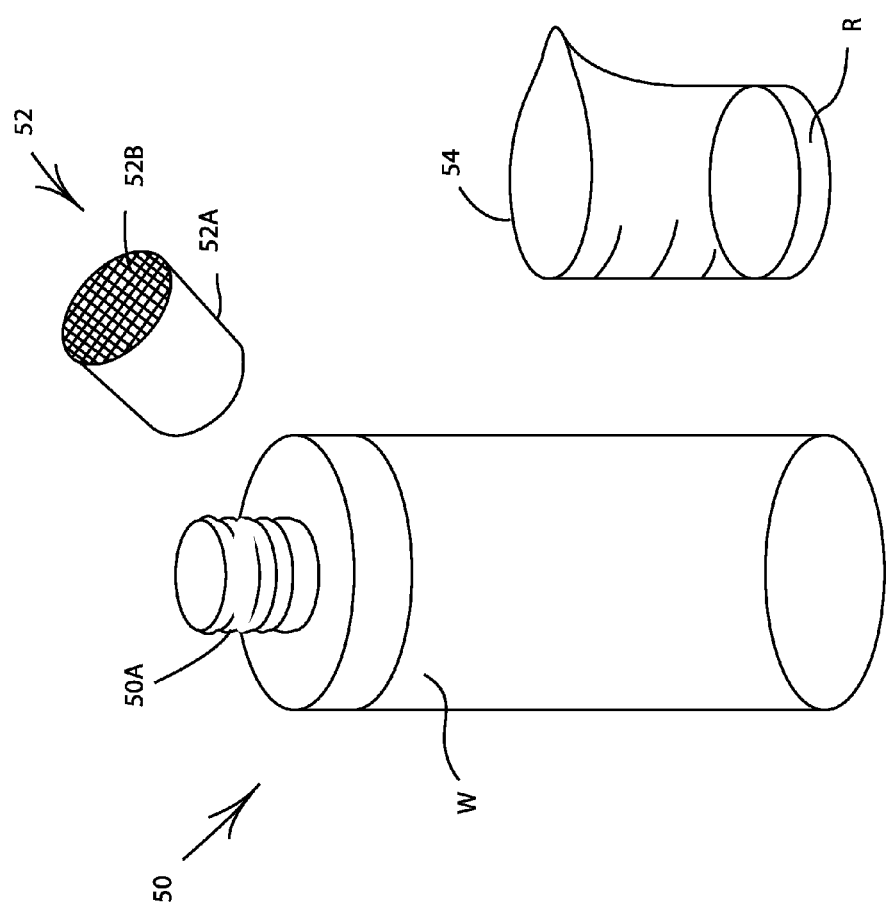
FIG. 2 is a perspective view of the preferred sample bottle with its inventive filter cap removed and of one of the several beakers preferably included with the apparatus.
Figure 3:
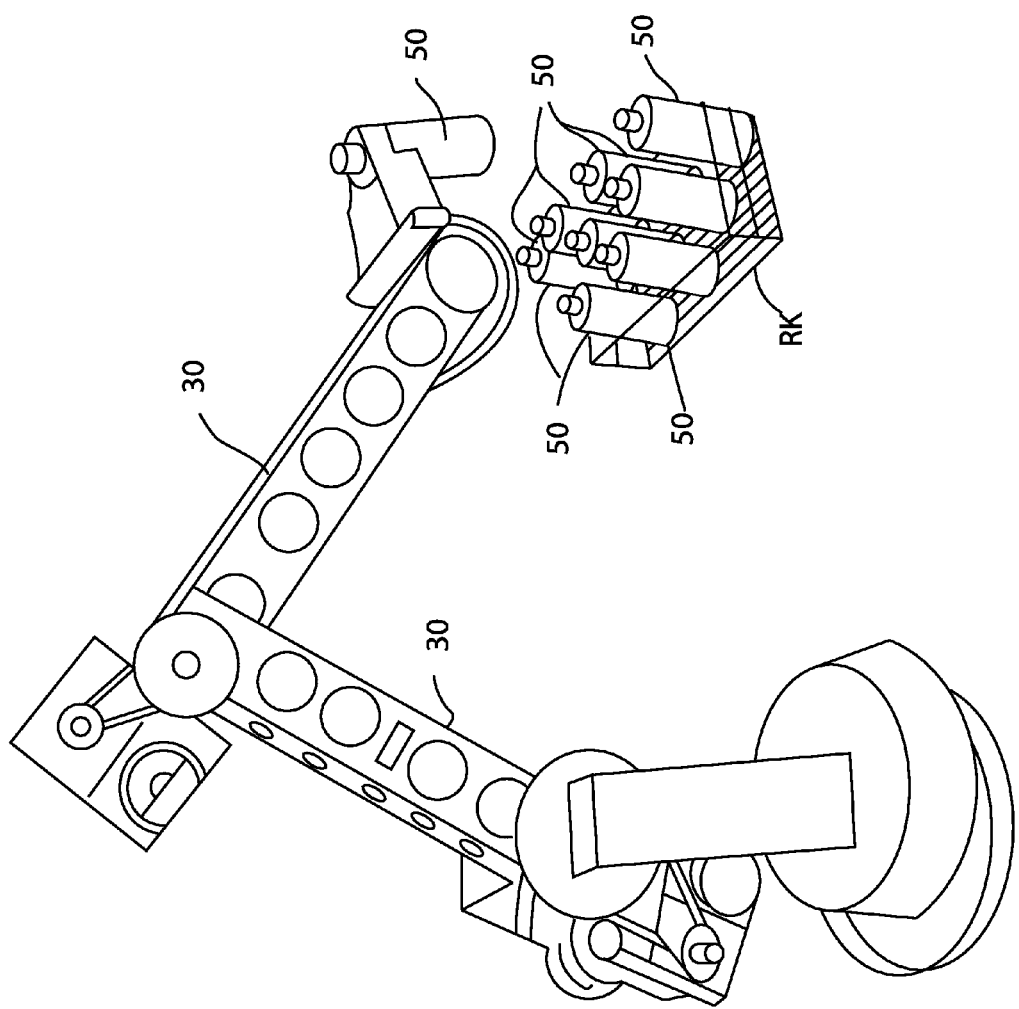
FIG. 3 is a perspective view of the preferred robotic arm lifting one of the sample bottles from a rack of sample bottles to pour sample water into the beakers.
Figure 4:
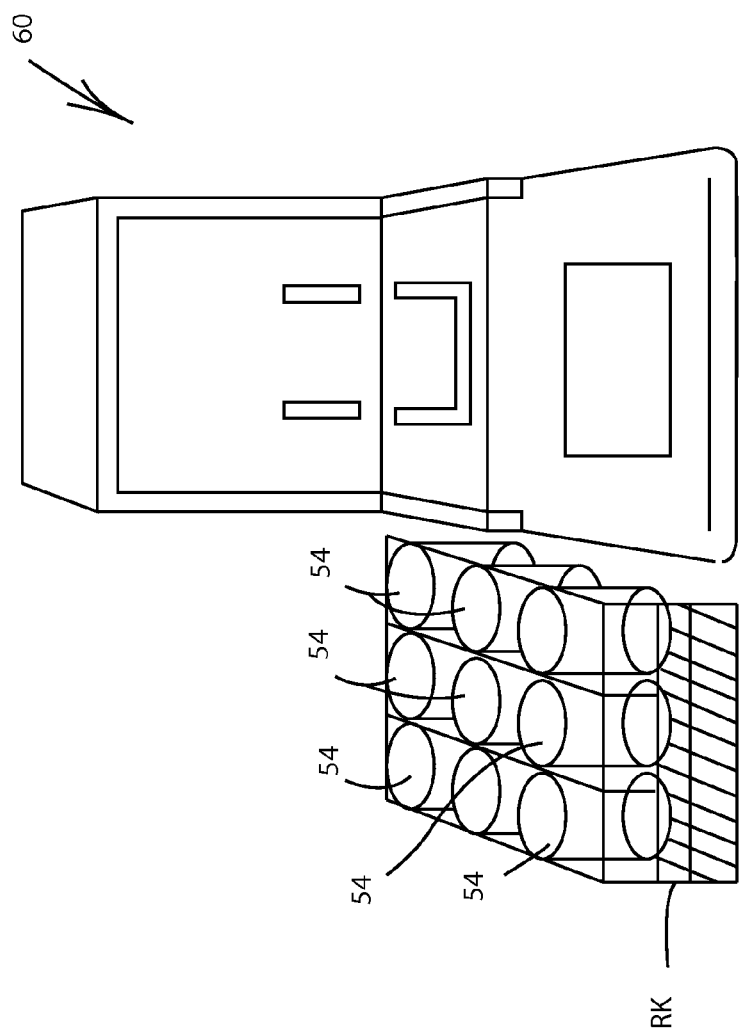
FIG. 4 is a perspective view of a preferred analytical balance scale, shown next to a rack of beakers.
Figure 5:
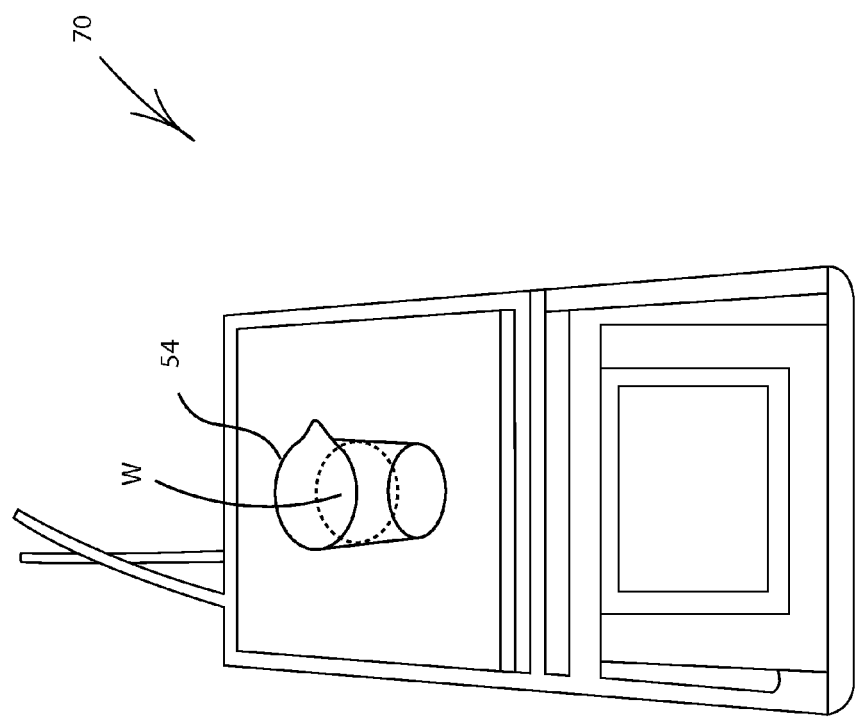
FIG. 5 is a perspective view of a preferred top loader balance scale.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Referring to FIG. 1-5, a water testing apparatus 10 is disclosed including a computer 20 containing a database D and an inventive water testing computer program P in operational communication the database D and with a robotic arm 30 having a gripper 32, a conductivity meter 40 having a meter electrode 40A, an analytical scale 60 which records and stores multiple weights in the computer database, a top loader balance 70, an oven 80, and further including a water sample bottle 50 with threaded opening 50A preferably sized to contain 250 cubic centimeters preferably formed of polyethylene and fitted with a removable filter cap 52 having an internally threaded cap rim 52A and filter mesh 52B across the top end of the cap rim 52A; a plurality of testing vessels which preferably are beakers 54; and a desiccator enclosure 90. The filter mesh 52B preferably is nominal, average size, preferably 2 micron size. The plurality of beakers 54 preferably is a rack RK of beakers 54.

The oven 90 door and desiccator enclosure 90 door each are preferably electro-gravity operated, and alternatively may be entirely electrically operated. For electro-gravity operation, the oven 80 and desiccator enclosure 90 are each mounted on four short legs. The legs on two diagonally opposed device corners can be electrically extendable and retractable to alternately cause forward and rearward device tilting. Extending the extendable rear leg while retracting the forward extendable leg tilts the device forwardly so that the device door can swing open and the robotic arm 30 can either place a beaker 54 or other item into or remove it from the interior of the device. Then retracting the extendable rear leg and extending the extendable front leg tilts the device backward, so that the device door can swing closed. A door stop structure is provided on each device to prevent the device door from opening to or beyond a fully perpendicularly position relative to the front of the device, so that tilting the device back will cause the door to swing closed rather than further open. The extension and retraction mechanisms of these legs can include a solenoid co-axial with the leg to drive the leg outwardly, or an electric motor rotating the leg which is externally threaded within a threaded leg passageway so that the leg advances outwardly or inwardly depending on the direction of its rotation by the motor, and is controlled by the computer 20 and the present program. This extendable leg arrangement has been found by applicant to be more practical than using the robotic arm 30 to pivot these doors.

Examples of either preferred or uniquely suited devices combined to create the present apparatus 10 are: the ST ROBOTICS™ robotic arm Model R17HP, the ROBOTIQ™ robotic gripper Model GC-001-ENIP, the HEWLETT PACKARD™ computer workstation Model xw 4600, SARTORIUS™ analytical balance Model MSA1245-100-DA, the SARTORIUS™ top loading balance Model MSA1202S-100-DO, VWR™ oven Model 414005-108 with electro-gravity operated door, and the AG conductivity meter Model 108.

Method

Figure 6:
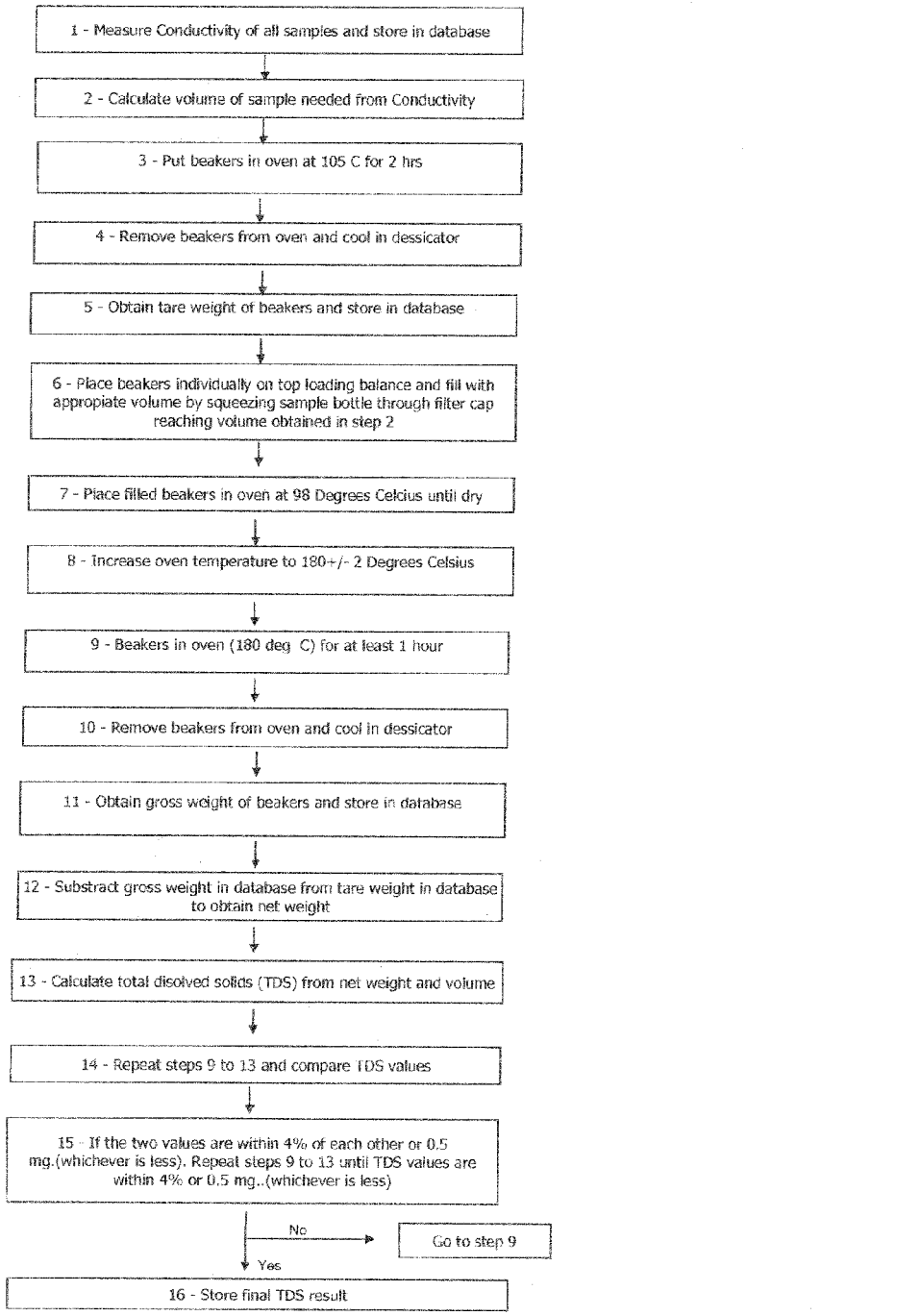
FIG. 6 is a block diagram of the preferred water testing method, most of which is a flow chart for the inventive computer program automating the method.

In practicing the invention, the following method may be used. See FIG. 6. The preferred method includes the steps of: providing the apparatus 10; a person or the robotic arm delivering sample water W into the sample bottle 50; the computer operating the robotic arm 30 to cause the robotic arm to grasp the meter electrode 40A and inserting the meter electrode 40A into the water sample W; the computer 20 operating the robotic arm to cause the robotic arm to sequentially place the at least one vessel and preferably a plurality of clean beakers 54 into the oven 80; the computer 20 signaling the oven 80 to heat to a first temperature for a first length of time to evaporate any moisture on or within the beakers 54; the computer 20 operating the robotic arm 30 to cause the robotic arm 30 to remove the beakers 54 from the oven 80 and to place the beakers 54 sequentially into the desiccator enclosure 90 for a length of time; the computer 20 operating the robotic arm 30 to cause the robotic arm 30 to place the beakers 54 one at a time onto the analytical scale 60 to record the tare weight and to store the tare weight of each beaker 54 in the database D; the robotic arm 30 placing each tared beaker 54 on the top loader balance 70 one at a time; computer 20 operating the robotic arm 30 to cause the robotic arm 30 to pick up the sample bottle 50 and move the sample bottle 50 toward a first one of the beakers 54 resting on the top loader balance 70; computer 20 operating the robotic arm 30 to cause the robotic arm 30 to rotate sample bottle 50, preferably a partial rotation from vertical in opposing directions three times, to mix the water sample and inverting the sample bottle 50 over the first beaker 54; computer 20 operating the robotic arm 30 to cause the robotic arm gripper 32 to then proportionately squeeze the sample bottle 50 while the computer 20 monitors the weight of the water on the top loader balance scale 70 as the sample water W enters the first beaker 54 in real time; computer 20 operating the robotic arm 30 to cause the gripper 32 to terminate the squeezing of sample bottle 50 once a desired volume of sample water W is reached in the first beaker 54; the computer causing the robotic arm 30 to sequentially repeat these beaker 54 filling steps for each successive beaker 54 to fill a plurality of the beakers 54; the computer operating the robotic arm 30 to cause the robotic arm 30 to place each of the beakers 54 into the oven 80 to evaporate the water W from each beaker 54; the computer 20 operating the oven 80 to increase the oven 80 internal temperature to a second temperature for a second length of time, thereby heating the beakers 54 and residue R within the beakers 54 to the second temperature and permitting the beakers 54 to remain heated at the second temperature until all water is evaporated from the beakers 54; the computer operating the robotic arm 30 to remove the beakers 54 from the oven 80 and place the beakers 54 into the desiccator enclosure 90 to cool to the balance temperature; the computer operating the robotic arm 30 to place the beakers 54 one at a time onto the top loader balance scale 70; the computer 20 receiving weight transmitted by the top loader balance 70 of each successive beaker 54 and its corresponding contained residue R to the database D; the computer 20 subtracting the tare weight of each beaker 54 to calculate the net weight of the residue R in each beaker 54; the computer 20 calculating the total dissolved solids (TDS) from the net weight and volume for each beaker 54; the computer 20 repeating the weighings of each beaker 54 to obtain constant weights for each beaker 54 according to criteria stored in the database D; once the constant weight criteria is met for each beaker 54, the computer 20 using the most recent weight to calculate the final TDS, and storing and recording the final TDS for each beaker 54 in the database D.

The volume needed for the test (in milliliters) is 25000/ conductivity in micromhos. The first temperature preferably is substantially 105 degrees Celsius. The first length of time preferably is substantially two hours. The second temperature preferably is 98 degrees Celsius for a second length of time, which is however long is needed for the beakers to become completely dry, which normally is several hours. Then the temperature is raised to 180 degrees Celsius for a third length of time of one hour to drive off any occluded moisture. The calculation of total dissolved solids (TDS) from the net weight and volume taken preferably is made according to the formula: TDS ((mg/1=(A−B)×1000/sample volume (in grams)).

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A method of testing water to determine concentrations of dissolved solids, comprising the steps of:
   providing a testing apparatus comprising a sample bottle fitted with a removable cap and having a filter comprising a filter mesh, a plurality of testing vessels, a desiccator enclosure, a computer containing a database and a water testing computer program in operational communication the database, a computer operated robotic arm having a gripper in communication with the computer, a computer operated conductivity meter having a meter electrode and in communication with the computer, a computer operated scale for recording and storing weights in the computer database, and a computer operated oven in communication with the computer;
   one of a person or the computer operated robotic arm delivering a first water sample into the sample bottle and securing the removable cap onto the sample bottle;
   the robotic arm grasping the meter electrode and inserting the electrode into the water sample;
   the conductivity meter relaying sample water conductivity data to the database;
   the robotic arm sequentially placing the at least one of the testing vessels into the oven;
   the computer signaling the oven to heat to a first temperature for a first length of time to thereby evaporate any moisture on or within the testing vessels;
   the robotic arm removing the testing vessels from the oven;
   the robotic arm placing the testing vessels sequentially into the desiccator enclosure;
   the robotic arm placing the testing vessels one at a time onto the analytical scale to transmit to the database and record the tare weight;
   the robotic arm placing each tared testing vessel on the scale one at a time;
   the robotic arm lifting the sample bottle and moving the sample bottle toward a first one of the testing vessels on the scale;
   the robotic arm moving the sample bottle to mix the water sample;
   inverting the sample bottle over the first one of the testing vessels;
   the robotic arm gripper then proportionately squeezing the sample bottle while the computer monitors the weight of the testing vessel and sample water as the sample water enters the first testing vessel;
   the gripper discontinuing the sample bottle squeezing once a desired volume of sample water is reached in the first testing vessel;
   the computer operating the robotic arm to sequentially repeat these testing vessel filling steps to fill a plurality of additional testing vessels;
   the computer operating the robotic arm to grip, lift and place the testing vessels into the oven;
   the computer operating the oven to increase its internal temperature to a second temperature to evaporate the water from the testing vessels, leaving residue in the testing vessels;
   heating the testing vessels and the residue within the testing vessels to the second temperature and permitting the testing vessels to remain heated at the second temperature until all of the water in the testing vessel is evaporated;
   the robotic arm removing the testing vessels from the oven;
   and placing the testing vessels into the desiccator enclosure to cool to a temperature of the balance;
   the robotic arm placing the testing vessels one at a time onto the scale;
   the scale transmitting the weights of each successive testing vessel and its corresponding contained residue to the database;
   the computer calculating the net weight of the residue in each testing vessel by subtracting the tare weight of the corresponding testing vessel;
   the computer calculating the quantity of total dissolved solids from the net weight and volume for each testing vessel;
   the computer repeating the weighings of each testing vessel to obtain constant weights according to stored criteria for each testing vessel;
   and, once the constant weight criteria is met for each testing vessel, the computer using the most recent weight to calculate the final total dissolved solids and storing and recording the final total dissolved solids for each testing vessel in the database.

2. The method of claim 1, wherein the scale is at least one of an analytical scale and a top loader balance scale.

3. The method of claim 1, wherein the volume of sample water for the test in milliliters is substantially 25000/conductivity in micromhos.

4. The method of claim 1, wherein the first temperature is substantially 105 degrees Celsius.

5. The method of claim 1, wherein the first length of time is substantially two hours and the second temperature is substantially 98 degrees Celsius for a second length of time, which is however long is needed for the testing vessels to become completely dry; then the temperature is raised to 180 degrees Celsius for a third length of time of substantially one hour to drive off any occluded moisture.

6. The method of claim 1, wherein the calculation of total dissolved solids (TDS) from the net weight and volume taken is made according to the formula: TDS mg/liter=(A−B)×1000/sample volume in grams.

7. A method of testing water to determine concentrations of dissolved solids, comprising the steps of:

providing a testing apparatus comprising a sample bottle fitted with a removable cap having a cap rim and having a filter comprising a filter mesh, a plurality of testing vessels, a desiccator enclosure, a computer containing a database and a water testing computer program in operational communication the database, a computer operated robotic arm having a gripper in communication with the computer, a computer operated conductivity meter having a meter electrode and in communication with the computer, a computer operated scale for recording and storing weights in the computer database, and a computer operated oven in communication with the computer;

one of a person or the computer operated robotic arm delivering a first water sample into the sample bottle and securing the removable cap onto the sample bottle;

the conductivity meter relaying sample water conductivity data to the database;

the robotic arm sequentially placing the at least one of the testing vessels into the oven;

the computer signaling the oven to heat to a first temperature for a first length of time to thereby evaporate any moisture on or within the testing vessels;

the robotic arm removing the testing vessels from the oven;

the robotic arm placing the testing vessels sequentially into the desiccator enclosure;

the robotic arm placing the testing vessels one at a time onto the analytical scale to transmit to the database and record the tare weight;

the robotic arm placing each tared testing vessel on the scale one at a time;

the robotic arm lifting the sample bottle and moving the sample bottle toward a first one of the testing vessels on the scale;

the robotic arm moving the sample bottle to mix the water sample;

inverting the sample bottle over the first one of the testing vessels;

the computer operating the robotic arm to sequentially repeat these testing vessel filling steps to fill a plurality of additional testing vessels;

the computer operating the robotic arm to grip, lift and place the testing vessels into the oven;

the computer operating the oven to increase its internal temperature to a second temperature to evaporate the water from the testing vessels, leaving residue in the testing vessels;

heating the testing vessels and the residue within the testing vessels to the second temperature and permitting the testing vessels to remain heated at the second temperature until all of the water in the testing vessel is evaporated;

the robotic arm removing the testing vessels from the oven;

the scale transmitting the weights of each successive testing vessel and its corresponding contained residue to the database;

the computer calculating the net weight of the residue in each testing vessel by subtracting the tare weight of the corresponding testing vessel;

the computer calculating the quantity of total dissolved solids from the net weight and volume for each testing vessel;

the computer repeating the weighings of each testing vessel to obtain constant weights according to stored criteria for each testing vessel;

and, once the constant weight criteria is met for each testing vessel, the computer using the most recent weight to calculate the final total dissolved solids and storing and recording the final total dissolved solids for each testing vessel in the database.

8. The method of claim 7, comprising the additional step of the robotic arm grasping the meter electrode and inserting the electrode into the water sample.

9. The method of claim 7 comprising the additional steps of the robotic arm gripper then proportionately squeezing the sample bottle while the computer monitors the weight of the testing vessel and sample water as the sample water enters the first testing vessel; and the gripper discontinuing the sample bottle squeezing once a desired volume of sample water is reached in the first testing vessel.

10. The method of claim 7, comprising the addition al step of placing the testing vessels into the desiccator enclosure to cool the testing vessels to the temperature of the balance; and the robotic arm placing the testing vessels one at a time onto the scale.

11. The method of claim 7, wherein said testing vessels are beakers.

* * * * *